US010507465B2

(12) United States Patent
Kaigala et al.

(10) Patent No.: US 10,507,465 B2
(45) Date of Patent: *Dec. 17, 2019

(54) MICROFLUIDIC PROBE WITH BYPASS AND CONTROL CHANNELS

(71) Applicant: International Business Machines Corporation, Armonk, NY (US)

(72) Inventors: Govind Kaigala, Zürich (CH); Robert Dean Lovchik, Zürich (CH); David Taylor, Zürich (CH)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/856,174

(22) Filed: Dec. 28, 2017

(65) Prior Publication Data

US 2018/0318832 A1 Nov. 8, 2018

Related U.S. Application Data

(63) Continuation of application No. 15/588,612, filed on May 6, 2017.

(51) Int. Cl.
*B01L 3/00* (2006.01)
*B01L 3/02* (2006.01)
*G01N 35/10* (2006.01)

(52) U.S. Cl.
CPC ......... *B01L 3/50273* (2013.01); *B01L 3/0293* (2013.01); *B01L 3/502715* (2013.01);
(Continued)

(58) Field of Classification Search
CPC .... B01L 3/022; B01L 3/02; B01L 3/00; B01L 3/502715; B01L 3/5027; B01L 3/502; B01L 3/50
(Continued)

(56) References Cited

U.S. PATENT DOCUMENTS 8,695,639 B2 4/2014 Delamarche et al.
9,207,684 B2 12/2015 Delamarche et al.
(Continued)

FOREIGN PATENT DOCUMENTS

WO  WO 2011/067670 A2 *  6/2011 ............. B01L 3/022
WO     2015132686 A1      9/2015
WO  WO 2016/128543 A1 *  8/2016 ............... B01L 3/02

OTHER PUBLICATIONS

Perrault CM et al., Integrated Microfluidic Probe Station, Rev. Sci. Instrum Nov. 2010, 81(11), pp. 115107-1 through 115107-8.
(Continued)

*Primary Examiner* — Christine T Mui
(74) *Attorney, Agent, or Firm* — Daniel P. Morris; Otterstedt, Walllace & Kammer, LLP

(57) ABSTRACT

A microfluidic probe includes a probe head with a processing surface that includes a first aperture and a second aperture. The probe further includes a liquid injection channel, which leads to the first aperture, and a liquid aspiration channel, which extends from the second aperture. The probe also includes a bypass channel, arranged so as to fluidly connect the liquid injection channel to the liquid aspiration channel, as well as a control channel. The latter fluidly connects to the bypass channel, hence forming a junction therewith, so as to define two portions of the bypass channel. These portions includes: a first portion that extends from the junction to the liquid injection channel; and a second portion that extends from that same junction to the liquid aspiration channel. The invention is further directed to methods of operation of a probe as described above, to process a surface.

6 Claims, 12 Drawing Sheets

(52) U.S. Cl.
CPC . *B01L 2200/027* (2013.01); *B01L 2200/0605* (2013.01); *B01L 2300/0861* (2013.01); *B01L 2300/0887* (2013.01); *B01L 2400/0487* (2013.01); *G01N 2035/1034* (2013.01)

(58) Field of Classification Search
USPC .......................................... 422/502, 500, 50
See application file for complete search history.

(56) References Cited

U.S. PATENT DOCUMENTS

| | | |
|---|---|---|
| 9,429,500 B2 | 8/2016 | Fowler et al. |
| 2015/0377753 A1 | 12/2015 | Toner et al. |
| 2016/0038940 A1 | 2/2016 | Babcock |
| 2016/0158750 A1 | 6/2016 | Putnam et al. |
| 2016/0243549 A1 | 8/2016 | Autebert et al. |

OTHER PUBLICATIONS

Xander F. et al., Passive Removal of Immiscible Spacers From Segmented Flows in a Microfluidic Probe, Applied Physics Letters 106, 074102 (2015); doi: 10.1063/1.4913202, pp. 074102-1 through 074102-5 plus cover.

Govind Kaigala et al. unpublished U.S. Appl. No. 15/588,612, filed May 6, 2017 Microfluidic Probe With Bypass and Control Channels pp. 1-35 plus 12 sheets drawings.

Paul J. Otterstedt, List of IBM Patents or Patent Applications Treated as Related, pp. 1-2. May 6, 2018.

* cited by examiner

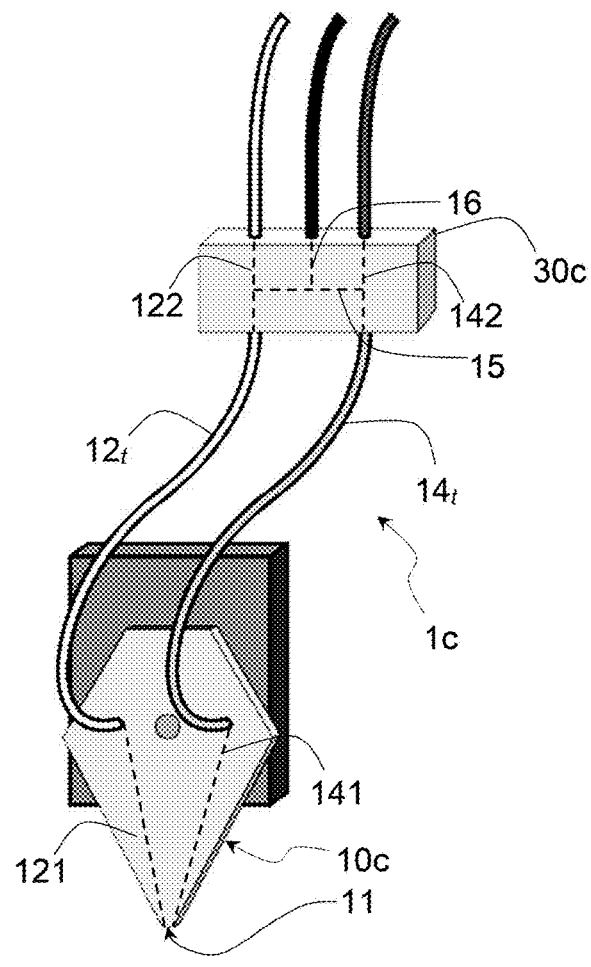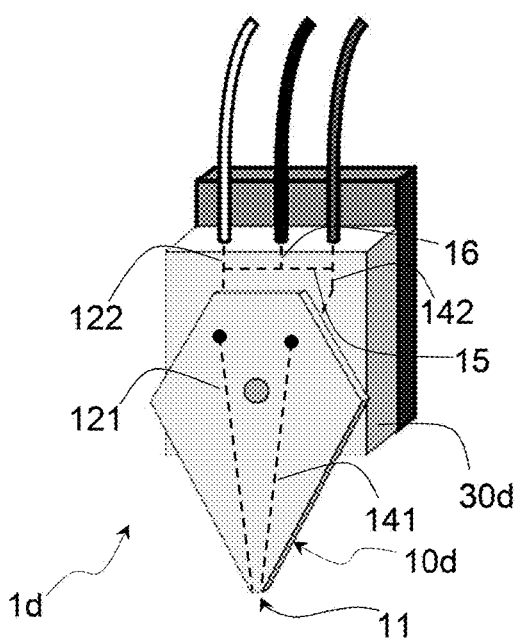
FIG. 9
FIG. 10

MICROFLUIDIC PROBE WITH BYPASS AND CONTROL CHANNELS

CROSS-REFERENCE TO RELATED APPLICATIONS

This application is a continuation of U.S. patent application Ser. No. 15/588,612 filed 6 May 2017, the complete disclosure of which is expressly incorporated herein by reference in its entirety for all purposes.

BACKGROUND

The invention relates in general to the field of microfluidics, microfluidic probe systems and microfluidic probe heads equipping such systems. In particular, it is directed to a microfluidic probe comprising liquid injection and aspiration channels, connected by a bypass channel, which is itself connected by a control channel.

Microfluidics deals with the precise control and manipulation of small volumes of fluids that are typically constrained to micrometer-length scale channels and to volumes typically in the sub-milliliter range. Prominent features of microfluidics originate from the peculiar behavior that liquids exhibit at the micrometer length scale. Flow of liquids in microfluidics is typically laminar. Volumes well below one nanoliter can be reached by fabricating structures with lateral dimensions in the micrometer range. Microfluidic devices generally refer to microfabricated devices, which are used for pumping, sampling, mixing, analyzing and dosing liquids. A microfluidic probe is a device for depositing, retrieving, transporting, delivering, and/or removing liquids, in particular liquids containing chemical and/or biochemical substances. For example, microfluidic probes can be used in the fields of diagnostic medicine, pathology, pharmacology and various branches of analytical chemistry. Microfluidic probes can also be used for performing molecular biology procedures for enzymatic analysis, deoxyribonucleic acid (DNA) analysis and proteomics.

A number of failure scenarios may occur when processing a surface with such microfluidic probes.

SUMMARY

According to a first aspect, the present invention is embodied as a microfluidic probe. The device comprises a probe head with a processing surface that comprises a first aperture (i.e., an injection aperture) and a second aperture (i.e., an aspiration aperture). The probe further includes a liquid injection channel, which leads to the first aperture, and a liquid aspiration channel, which extends from the second aperture. Remarkably, the probe also comprises a bypass channel, arranged so as to fluidly connect the liquid injection channel to the liquid aspiration channel, as well as a control channel. The latter fluidly connects to the bypass channel, hence forming a junction therewith, so as to define two portions of the bypass channel. These portions includes: a first portion that extends from said junction to the liquid injection channel; and a second portion that extends from that same junction to the liquid aspiration channel. The probe is preferably designed so as to allow a hydrodynamic flow confinement of processing liquid injected through the first aperture and aspirated from the second aperture.

The above structure makes the MFP technology robust against partial or complete blockage of one or several of its apertures, e.g., when the MFP head is in contact with the surface or while scanning the surface with the head. That is, in case of failure, the injected processing liquid can be diverted through the bypass channel, instead of leaving the probe, assuming a suitable liquid/pressure flow is applied to the control channel. There are indeed circumstances where one wants to avoid the processing liquid to uncontrollably escape the probe as this typically leads to a loss of confinement of the processing liquid and may then contaminate the immersion liquid and subsequently the substrate. As a further advantage, the above probe can be operated in constant flow mode or constant pressure mode.

In embodiments, the hydraulic resistance of the first portion of the bypass channel is larger than the hydraulic resistance of the second portion of the bypass channel, which makes it possible to limit the flow that can pass from the control channel through the injection aperture (e.g., in case the operating distance becomes excessively large). For example, the hydraulic resistance of the first portion may be between 2 and 100 times larger than the hydraulic resistance of the second portion.

In preferred embodiments, the first portion of the bypass channel has an average cross-section that is smaller than an average cross-section of the second portion of the bypass channel. This way, the resistances of the two channel portions can be easily varied, without requiring change in the surface material properties.

Yet, the first portion and the second portion of the bypass channel shall preferably have a same depth (which simplifies the fabrication process), while the first portion will have, on average, a smaller width than the second portion.

Preferably, the first portion of the bypass channel has a length that is larger than the length of the second portion of the bypass channel, so as to achieve a larger hydraulic resistance for the first portion.

Whereas the bypass channel portions may have different resistances, the liquid injection channel, the liquid aspiration channel and the control channel preferably have, each, a constant hydraulic resistance along their main channel extensions.

However, in preferred embodiments, the hydraulic resistance of the control channel is made smaller than the hydraulic resistance of each of the injection channel and the aspiration channel, to allow sufficient aspiration flow rates in practice.

Preferably, the bypass and control channels are provided directly in the probe head, to allow faster reaction times in case of failures. That is, each of the liquid injection channel, the liquid aspiration channel, the bypass channel and the control channel extends within a body of the probe head, so as for the bypass channel to fluidly connect, within the body, the liquid injection channel to the liquid aspiration channel. In variants, the bypass and control channels are provided in a bypass module, outside the probe head. Such an "off-chip" (or "off-head") configuration makes it possible to re-use existing probe heads.

In each case, the present probes may notably be equipped with probe heads of the so-called "vertical" type or, in variants, of the "horizontal" type. And in each case, the fabrication of the heads can be kept simple, involving a few layers of materials.

For example, in embodiments relying on a horizontal probe head that includes the bypass and control channels, the head may comprise two layers, i.e., a control layer and a routing layer, where a bottom face of the control layer covers a top face of the routing layer. The processing surface is defined by a bottom face of the routing layer, opposite to the top face thereof, whereby the first and second apertures are, each, defined on the bottom face of the routing layer.

Moreover, the routing layer comprises a first pair of through-vias extending through a thickness thereof, so as to form segments of the liquid injection channel and the liquid aspiration channel, in fluid communication with the first aperture and the second aperture, respectively. The routing layer further comprises the bypass channel, which is defined on the top face of the routing layer. The control layer comprises a through-via extending through a thickness thereof, so as to form a segment of the control channel. The control layer further includes a second pair of through-vias extending through a thickness thereof, so as to form additional segments of the liquid injection channel and the liquid aspiration channel, respectively, in fluid communication with said first pair of through-vias, respectively.

In embodiments where the probe head is configured as a vertical probe head, the latter preferably comprises two layers (at least) of materials. Each of the first segment of the liquid injection channel and the first segment of the liquid aspiration channel are grooved on one of these two material layers and closed by the other one of the other two material layers. The bypass and control channels may further be grooved on the same layer as the first segments of the injection and aspiration channels.

In embodiments where the bypass-concept is implemented outside the probe head, a first segment of the liquid injection channel and a first segment of the liquid aspiration channel may be defined on (or in) the probe head, so as to be in fluid communication with the first aperture and the second aperture, respectively. However, the probe further comprises a bypass module, which is distinct from the probe head, wherein the bypass module comprises the bypass channel and the control channel, as well as a second segment of the liquid injection channel and a second segment of the liquid aspiration channel. The bypass channel fluidly connects, within the bypass module, the second segment of the liquid injection channel to the second segment of the liquid aspiration channel. For completeness, the second segment of the liquid injection channel and the second segment of the liquid aspiration channel need be in fluid communication with the first segment of the liquid injection channel and the first segment of the liquid aspiration channel, respectively.

Preferably, the probe head is fixed to the bypass module, and the probe head comprises through-vias, so as for the second segment of the injection channel and the second segment of the aspiration channel to be in fluid communication with the first segment of the injection channel and the first segment of the aspiration channel, respectively.

In embodiments, the processing surface comprises a set of two or more second apertures, including said second aperture, wherein each of the two or more second apertures is arranged at a distance from the first aperture on the processing surface. In such cases, the probe comprises:
- a set of two or more liquid aspiration channels, including said liquid aspiration channel, wherein each of the two or more liquid aspiration channels extends from a respective one of the second apertures;
- a set of two or more bypass channels, including said bypass channel, each arranged so as to fluidly connect the liquid injection channel to a respective one of the liquid aspiration channels; and
- a set of two or more control channels, including said control channel, each fluidly connecting to a respective one of the two or more bypass channels, so as to allow processing liquid injected via the injection channel to be diverted through the bypass channels, if needed.

In embodiments, the second aperture comprises a slit, shaped so as to partly extend around the first aperture on the processing surface. Yet, the first aperture is not completely surrounded by the slit on the processing surface.

In embodiments, the probe comprises a plurality of bypass channels, including said bypass channel, each arranged so as to fluidly connect the liquid injection channel to the liquid aspiration channel. Having multiple bypass channels allows a gradual diversion of the processing liquid, when necessary. It further allows the device to have different working points, i.e., different bypass thresholds can be set, which makes it possible to cope with different failure scenarios with a same device, operated in a fully passive mode.

Preferably, the probe is configured to operate in one or each of two modes, the latter including:
- a constant liquid flow mode, wherein a constant liquid flow is applied to each of the liquid injection channel, the liquid aspiration channel, and the control channel; and
- a constant pressure actuation mode, wherein a constant pressure is applied to each of the liquid injection channel, the liquid aspiration channel and the control channel.

According to another aspect, the invention can be embodied as a method of operating a probe such as described above. Basically, this method comprises: positioning the probe head in proximity with a sample surface to be processed, so as for the processing surface to face the sample surface; and injecting processing liquid via the first aperture while aspirating liquid from the second aperture, to process the sample surface.

In typical applications, the probe head is positioned in proximity with an immerged sample surface. I.e., an immersion liquid covers that surface, so as for the probe head to be at least partly immersed in the immersion liquid. As a result, some of this immersion liquid gets typically aspirated from the second aperture. Preferably, the liquid injection and aspiration are performed so as to maintain a hydrodynamic flow confinement of injected liquid between the injection aperture and the aspiration aperture.

Processing the surface may lead to block one or each of the first aperture and the second aperture, due to a proximity of the probe head with the sample surface processed. As per the design of present probes, the processing liquid injected via the injection channel may nevertheless pass through the bypass channel and be aspirated via the aspiration channel.

In preferred embodiments, the present probes are used as passive systems. However, in variants, they may be dynamically controlled, which may basically require to adjust a liquid flow rate or a liquid pressure in the control channel, in operation. Still, one understands that adjusting the liquid flow rate in the control channel likely impacts the liquid pressure(s) in other channels and, conversely, adjusting the pressure in the control channel typically impacts the various liquid flow rates.

In passive systems, the liquid flow rate or the liquid pressure may be adjusted (e.g., once for all) prior to positioning the probe head in proximity with the sample surface. Then, the liquid flow rate or the liquid pressure is kept constant in the control channel, while injecting the processing liquid via the first aperture and aspirating liquid from the second aperture to process the sample surface.

Devices, apparatuses, systems and methods embodying the present invention will now be described, by way of non-limiting examples, and in reference to the accompanying drawings.

BRIEF DESCRIPTION OF THE DRAWINGS

FIGS. 9-10 illustrate variants to the microfluidic probe system of FIG. 1, wherein the bypass channel is provided in a module distinct from the probe head, here assumed to be of the "vertical" type;

Figure 1:
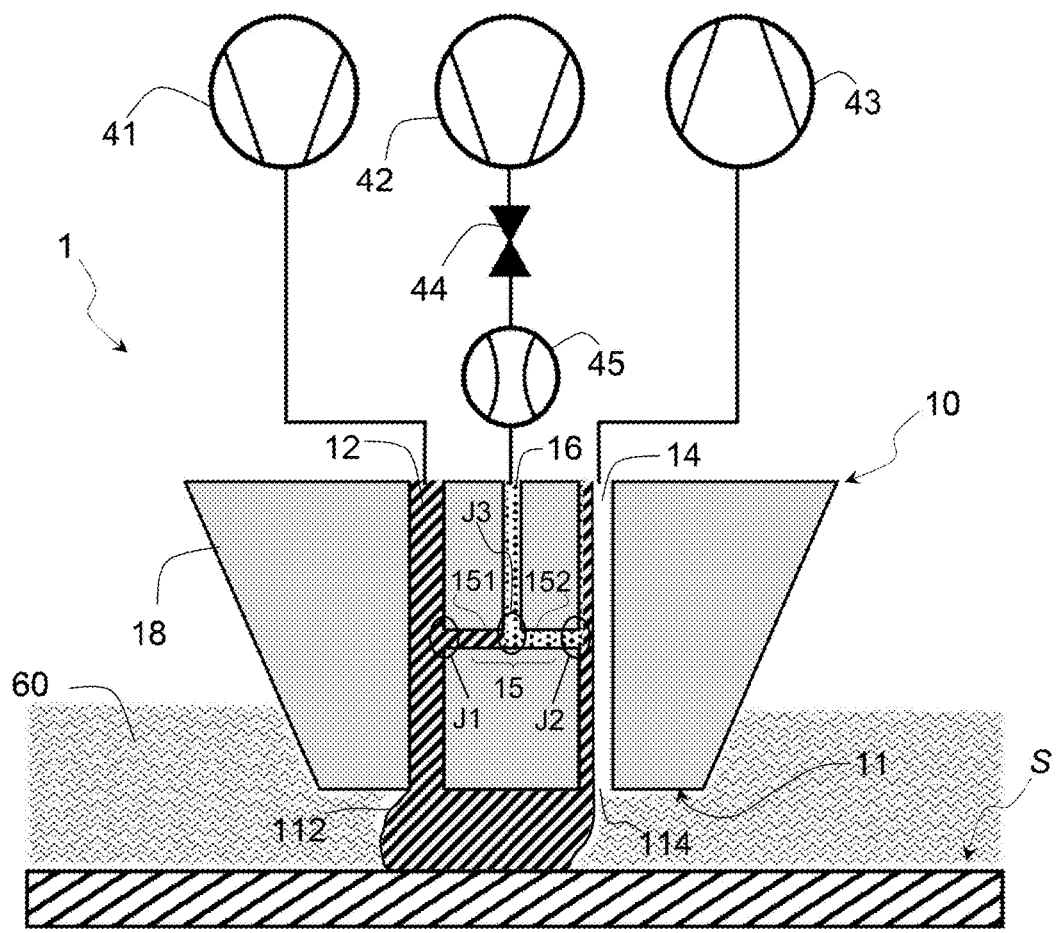
FIG. 1 depicts a microfluidic probe, according to embodiments. The probe comprises bypass and control channels provided directly in the probe head.
Figure 1:
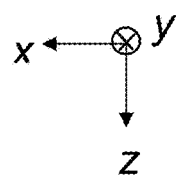

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

A unique feature of microfluidic probes (scanning, non-contact technology) is the possibility to localize the processing liquid on an immersed substrate, due to a hydrodynamic flow confinement (HFC) of the processing liquid in the immersion liquid. Ideally, what is needed for such a scanning probe technology to reliably operate is: (i) a constant probe-to-surface distance during the scanning, which, ideally, requires a surface free of substantial topographical variations; and (ii) no particulate contamination of the liquids both in the processing and immersion liquid, to avoid clogging the channels.

In practical implementations though, the probe-to-substrate distance (or "operating distance") can vary when scanning the probe head over the substrate. Typical variation amplitudes are of 0.1 mm. Such variations may result in temporary blocking one or several of the apertures of the device. This, as the present Inventors observed, may cause a break-down of the localization of the liquid flow, resulting in a contamination of the substrate by the processing liquid. In addition, particulates in the processing/immersion liquid flowing in the injection/aspiration channels can perturb the flow conditions, in particular, during extended periods of operation.

The present Inventors have therefore designed concepts of microfluidic probes (or MFPs) and operation methods that improve the robustness of the MFP technology. In particular, such concepts make the MFP technology more robust against partial or complete blockage of one or several apertures of the devices.

In reference to FIGS. 1-11, an aspect of the invention is first described, which concerns a microfluidic probe 1, 1a-1f. Microfluidic probes are sometimes referred to as microfluidic (or MFP) devices, apparatuses or systems in the literature. A microfluidic probes notably comprises a probe head (or MFP head), designed to come in contact with and process a sample surface. In addition, it typically comprises additional components needed to operate the MFP head, such as tubes, tubing ports, liquid tanks, pressure or vacuum sources, valves, additional MFP modules, etc.

As depicted in the accompanying drawings, the present probe concept includes a probe head 10, 10a-10h, which exhibits a processing surface 11, onto which are defined a first aperture 112 and a second aperture 114. The processing surface 11 typically forms a boundary of the probe head, e.g., a face of the head, meant to face the surface of the sample to be processed, in operation.

As usual in the art, the probe comprises a liquid injection channel 12, which leads to the first aperture 112, as well as a liquid aspiration channel 14, which extends from the second aperture 114. Thus, the apertures 112, 114 can be respectively regarded as a liquid injection aperture and a liquid aspiration aperture. The injection channel is used to inject liquid toward the surface S to be processed, i.e., to eject liquid from the first aperture 112, whereas the aspiration channel is used to (re-)aspirate liquid from the surface 5, in operation. This assumes that the probe is otherwise configured to allow liquid injection and liquid aspiration via the channels 12, 14.

Remarkably here, the probe further includes a bypass channel 15, which is arranged so as to fluidly connect the liquid injection channel 12 to the liquid aspiration channel 14. I.e., the bypass channel 15 physically connects, directly, to each of the injection channel 12 and the aspiration channel 14, so as to form respective junctions J1, J2 therewith, as depicted in FIG. 1.

In addition, the probe comprises a control channel 16, which fluidly connects to the bypass channel 15, hence forming a junction J3 therewith. I.e., there are at least three junctions J1, J2, J3 in total, one J3 formed between the control channel 16 and the bypass channel 15, in addition to the two junctions J1, J2 formed at the ends of the bypass channel 15 with the channels 12, 14. The junction J3 is typically located between the injection channel 12 and the aspiration channel 14, e.g., between the two junctions J1, J2.

The junction J3 formed between the control channel 16 and the bypass channel 15 implies distinct channel portions 151, 152 for the bypass channel 15, formed on each side of this junction J3. A first channel portion 151 extends from the junction J3 to the injection channel 12, while a second portion 152 extends from that same junction J3 to the aspiration channel 14. Thus, the two portions 151, 152 potentially enables fluid communication between each of the channels 12, 14 and a respective portion 151, 152 of the bypass channel 15 it connects to.

The extent to which fluid communication is enabled between the channels 12, 14 and their respective portions 151, 152 is governed by a number of parameters, as discussed below in detail. Yet, this can be controlled (at least partly) thanks to the control channel 16, assuming that the probe is configured to apply a liquid flow (or pressure) to this channel 16.

Figure 7:
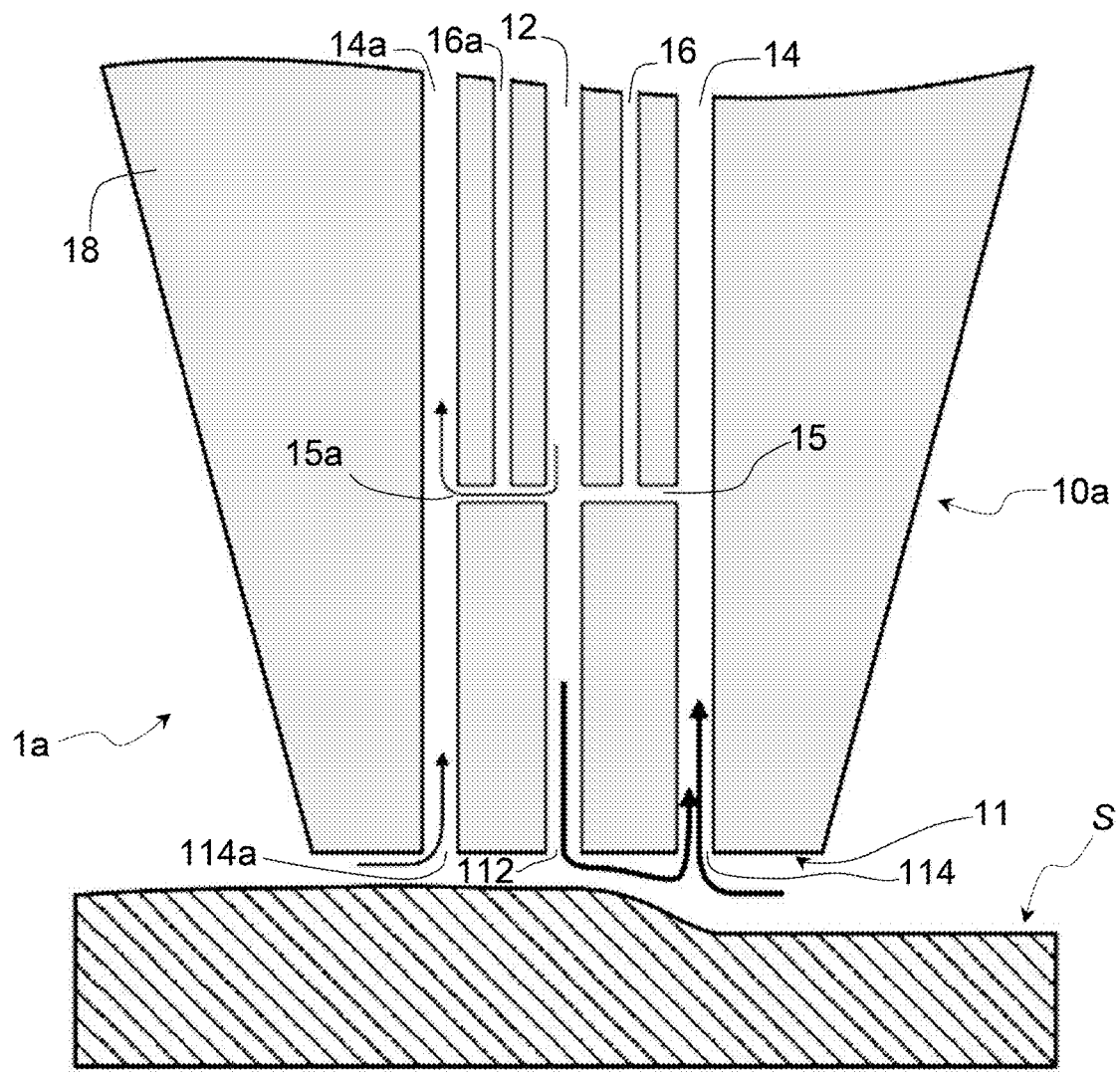
FIGS. 7-8 illustrate variants to the probe head of FIG. 1, which involve multiple bypass and/or control channels.
Figure 8:
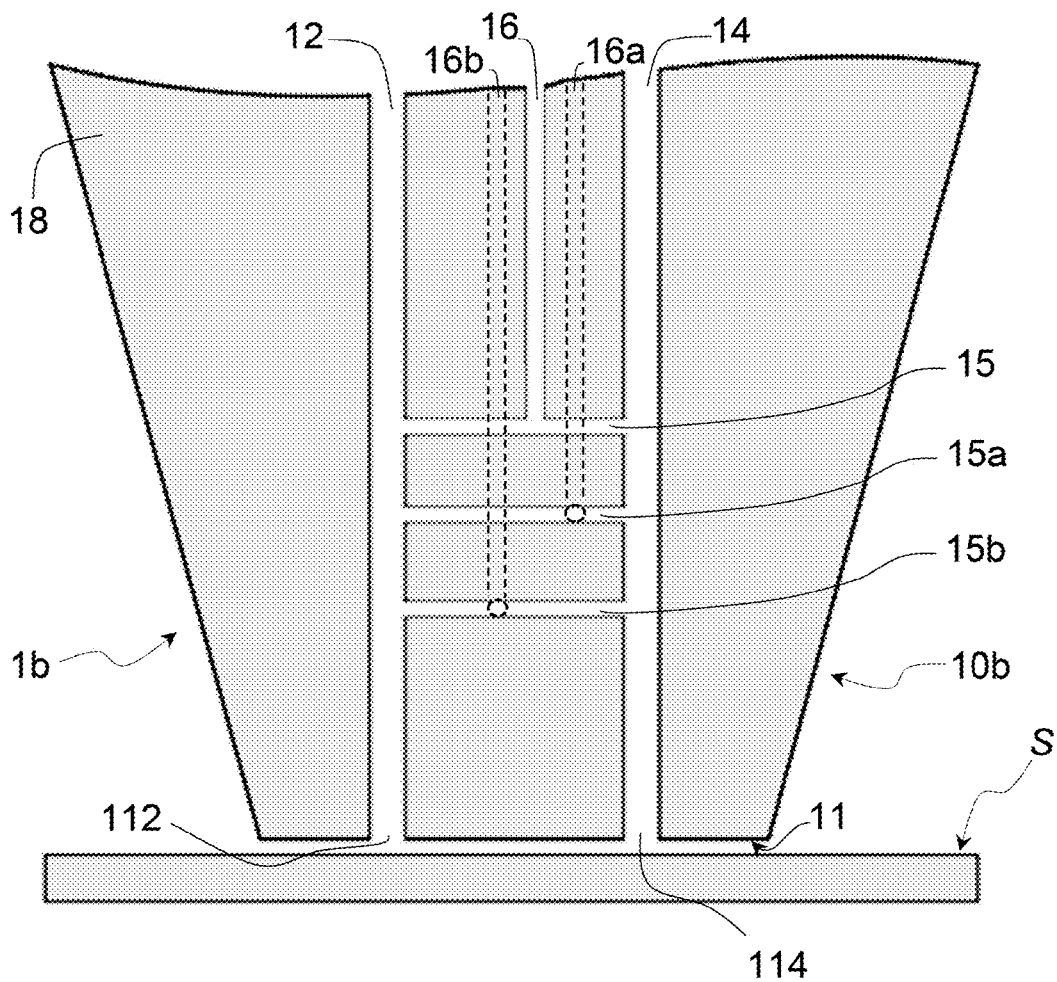
Figure 8:
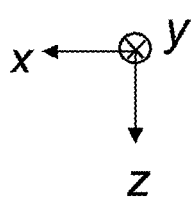

If necessary, more than one control channel may be provided, each connecting to a same or a respective bypass channel, in order to adapt the bypass properties or ensure sufficient control on a bypass channel, as latter discussed in reference to FIGS. 7-8. However, a single bypass channel and a single control channel already makes it possible to cope with various failure scenarios in practice.

The present probes are preferably configured so as to allow hydrodynamic flow confinement of the injected liquid, as assumed in most of the embodiments described below.

Thanks to the bypass channel 15 between the injection and aspiration channels 12, 14 and the control channel 16 connected thereto, the present concept makes the MFP technology robust against partial or complete blockage of one or several of the apertures of the head, e.g., when bringing the MFP head in contact with the surface processed or while scanning this surface with the head.

In normal operation (as assumed in FIG. 1), no processing liquid (as injected through channel 12) should pass through the entire bypass channel 15. To enable this normal mode of operation, the control channel 16 need to connect the bypass channel 15 at a junction J3 that is distinct from the two outer junctions J1, J2. That is, two well-defined portions 151, 152 of the bypass channel 15 need be defined on each side of the junction J3. In other words, each of the hydraulic resistances R4 and R5 (associated to respective portions 151, 152, see FIGS. 2A, 2B) is strictly greater than zero. This way, the pressure at the junction J3 can be matched to the pressure at the junction J1 between the injection channel 12 and the bypass channel 15, by varying the pressure in the control channel 16. This results in a stagnation of the liquid flow, i.e., no additional liquid may enter the bypass channel 15 from the injection channel 12 across the portion 151.

Figure 3:
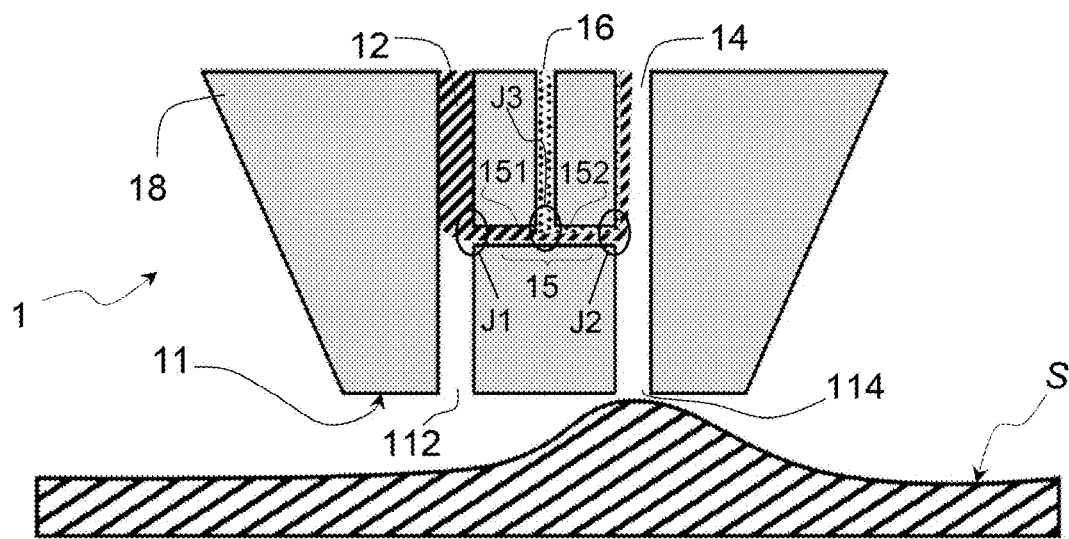
FIGS. 3-6 show side views of the same probe head, in operation, and illustrate how the bypass concepts operates in case of failure scenarios, as involved in embodiments.
Figure 4:
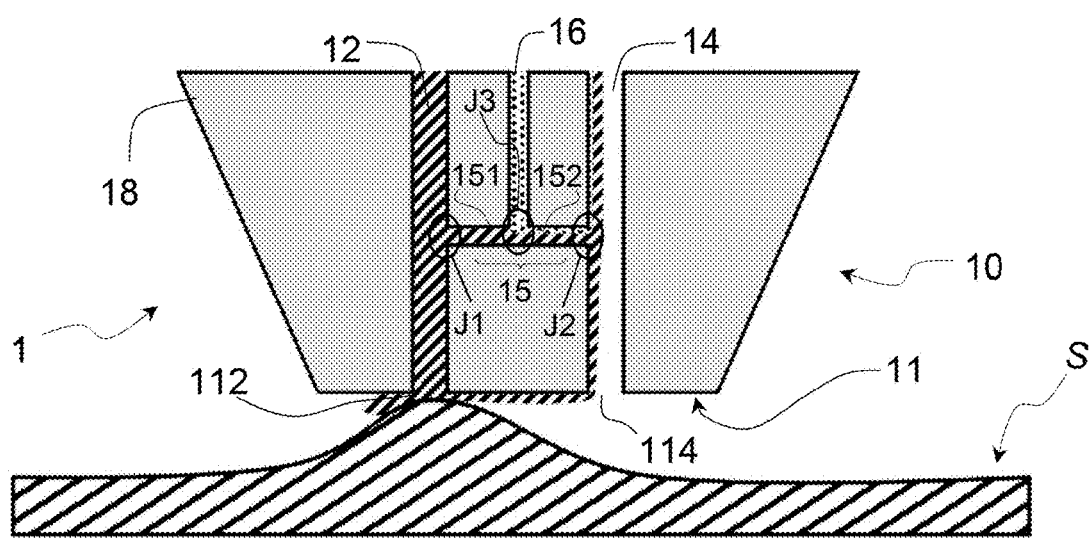
Figure 5:
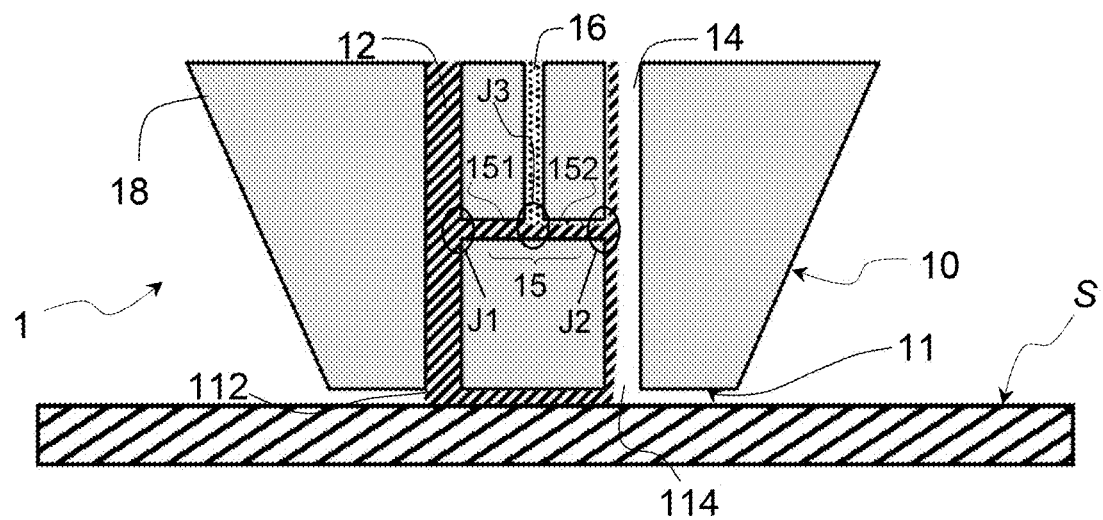
Figure 6:
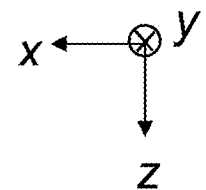
Figure 6:
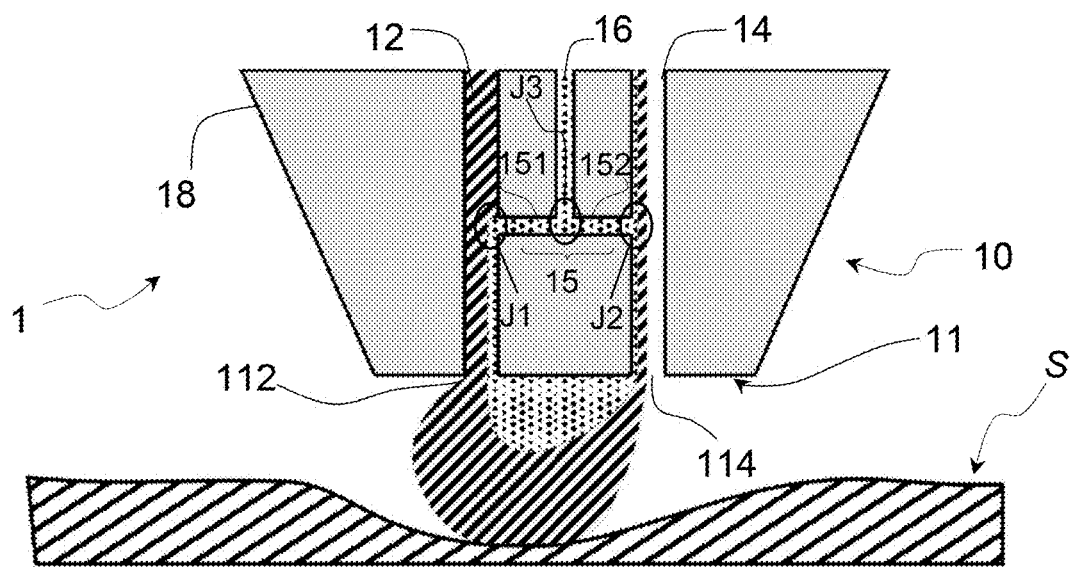

Yet, in case of failure (e.g., blockage of one or each of the apertures), the processing liquid can be passed through the entire bypass channel 15 (i.e., though both portions 151 and 152), instead of leaving the probe, as illustrated in FIGS. 3-5. There are indeed circumstances where one wants to avoid the processing liquid to escape the probe as this may typically lead to a loss of confinement of the processing liquid, which may then contaminate the immersion liquid and the substrate, as noted earlier.

The transition threshold between the normal operation and failure mode can be set by suitably adjusting the flow rate/pressure in the control channel 16 or the value of the hydraulic resistance R4+R5 of the bypass channel 15.

As it may further be realized, the present MFP concepts are compatible with a constant flow mode or a constant pressure mode of operation, which allow, each a fully passive operation of the probe head. That is, the probe can be operated in constant flow mode or in constant pressure mode. In constant pressure mode, liquid tanks would typically need be connected to the injection channel 12, the control channel 16 and the aspiration channel 14 (not shown). The pressure and vacuum levels applied 41-43 to said liquid tanks remain constant. In constant flow mode, a constant flow rate is maintained in the injection channel 12, the control channel 16 and the aspiration channel 14, by, e.g., employing a dedicated syringe pump to effect flow in these channels. A passive compensation for failures as described above occurs in both modes of operations in essentially the same manner.

Yet, the present approach allows active control of one or more of the various liquid flows involved. Thus, fully passive or fully active control schemes can be contemplated. Now, various intermediate schemes can be contemplated, involving only a partial control of the liquid flows (e.g., in the control channel 16 only). In addition, the present MFP concepts are further compatible with various head configurations and aperture designs, as exemplified in FIGS. 1, 7-14. Moreover, the bypass and control channels can be implemented directly on the head or in an external module 30 ("off-head"). All this is discussed below in detail in reference to specific embodiments.

Figure 2A:
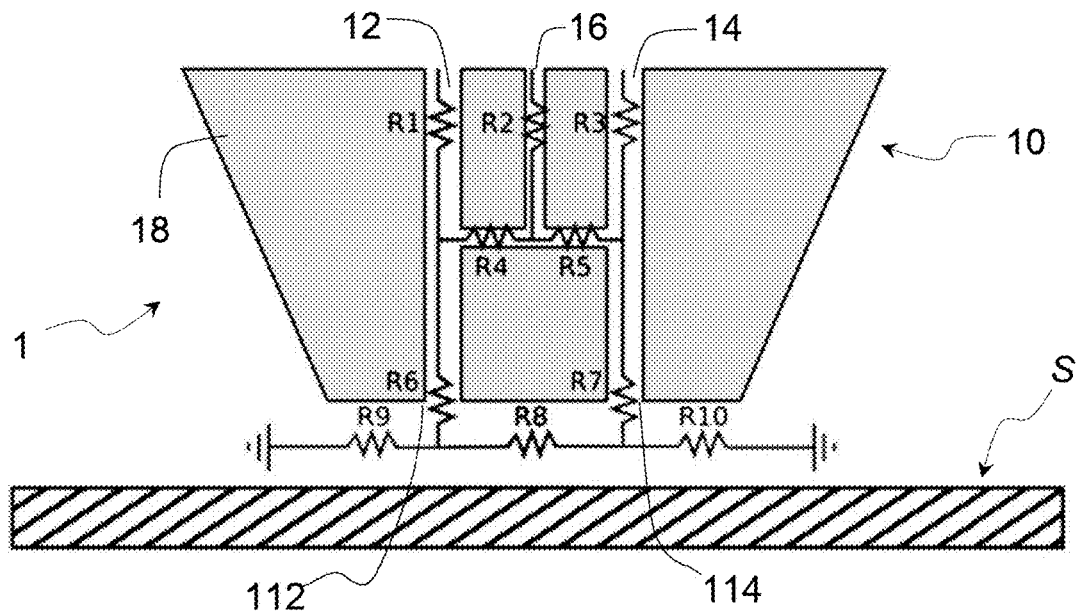
FIG. 2A shows a side view of a probe head as involved in FIG. 1—a corresponding circuit of hydraulic resistances of the various liquid flow paths is symbolically superimposed on the view.
Figure 2B:
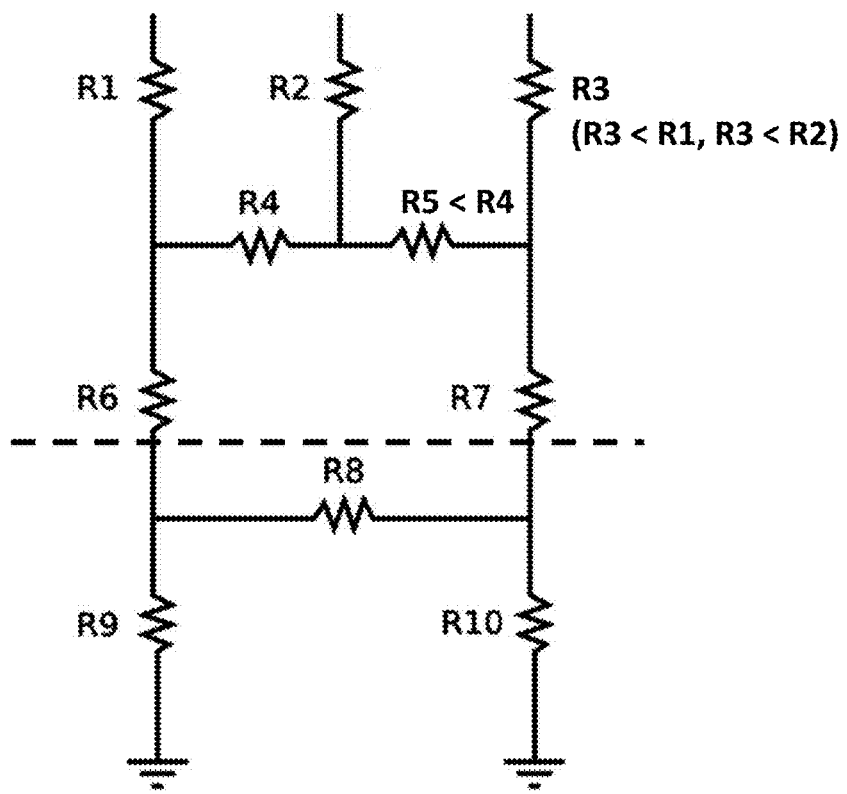
FIG. 2B depicts the same and additionally shows constraints between the hydraulic resistances, as involved in embodiments.

Referring now more particularly to FIGS. 2A and 2B, we note that there are at least two flow paths between the junctions J1, J2 formed between the bypass channel 15 and the injection channel 12 and the aspiration channel 14. Additional flow paths may exist in case more bypass channels are implemented or if the bypass channel 15 branches into several channels which are connected to the aspiration channel 14 at different locations. This would allow to have multiple bypass channels, which are dedicate to alter the flow path in case of specific failure events. In the most basic design featuring a single bypass channel, one flow path occurs along the bypass channel 15, which has a hydraulic resistance of R4+R5. A second flow path occurs between the apertures 112, 114, across the space between the probe head 1 and the surface S of the sample processed; it has a hydraulic resistance of R6+R8+R7. When typical design parameters are used for the channels 12, 14, 16 and apertures 112, 114, the hydraulic resistances of those two flow paths are in the same range, so that the entire flow of injected liquid can be passed through either of the two flow paths without significant deviations of the operating pressures. The resistances R8, R9, and R10 are resistances between the probe head 1 and the surface S. The resistance R8, for example, varies with the distance of the probe 1 from the surface S. Yet, the hydraulic resistance of the bypass channel 15 may be adjusted to a desired, normal operating distance. Conversely, the operating distance could also be adjusted, in some extent, depending on the resistance of the bypass channel 15.

At a standard operating distance (between the probe and the surface S), no liquid flowing through the injection channel 12 should enter the bypass channel 15 in order to minimize consumption of reagents. Consequently, typically an inexpensive buffer is injected in the control channel 16 to cause stagnation of flow in the portion 151 (between J1 and J3).

Now, when the distance between the probe 1 and the surface S of the sample deviates from the standard operating distance (as illustrated in FIGS. 3-6), the bypass and control channels cause the composition of the flow through the two flow paths evoked above to passively reconfigure. This, in turns, compensate for undesired consequences of excessively small and excessively large operating distances.

In case the operating distance becomes smaller than the standard operating distance (FIGS. 3-5), the value of R6+R7+R8 becomes larger than that of R4+R5 and the liquid flowing in the injection channel 12 is passively diverted to follow the path of lower resistance through the bypass channel 15. The proportion of the flow through the injection channel 15 that is redirected through the bypass channel 16 varies, depending on the operating distance. In case of full contact between the probe and the surface S (FIG. 5) or in case of blockage of the injection aperture 112 (FIG. 4) or the aspiration aperture 114 (FIG. 3), the entire processing liquid flow (through injection channel 12) is redirected through the bypass channel 15 to enter the aspiration channel 14. Thus, leakage of the processing liquid (e.g., into immersion liquid) can be prevented.

In case the operating distance becomes greater than the standard operating distance (as assumed in FIG. 6), the value of R6+R7+R8 becomes smaller than that of R4+R5 and the liquid flowing in the control channel 16 gets passively diverted to flow through the injection aperture 112. Hence, the flow through the injection aperture 112 increases and the volume occupied by the injected liquid in the space between the probe 1 and the surface S of the sample protrudes further downwards and partially compensates for the large operating distance.

The resistances in the injection channel 12, control channel 16 and aspiration channel 14 allow a precise control of the respective flow rates, e.g., by controlling the pressure in liquid tanks connected to those channels. The resistance values R1, R2 and R3 therefore depend on the desired range of flow rates and precision. Still, since the flow through the injection channel 12 and the control channel 16 will typically be comparable (if not equal) during standard operation, R3 can advantageously be made smaller (e.g., about five times smaller) than each of R1 and R2, to enable sufficient aspiration flow rates. We note, however, that the resistance R3 need not systematically be smaller than R1 or R2, e.g., when employing a syringe pump to effect flow in these channels 12, 16.

As further shown in FIG. 2B, the hydraulic resistance R4 of the bypass channel portion 151 is preferably made larger than the hydraulic resistance R5 of the second portion 152. As one may realize, this makes it possible to limit the flow that can pass from the control channel 16 through the injection aperture 112 in case the operating distance becomes larger than the standard operating distance. In such a scenario, if R4 is too small, the flow of liquid injected through the injection aperture 112 can be so high that the injected liquid is not aspirated back through the aspiration aperture 114, hence contaminating the surrounding immersion liquid.

Whenever possible, the head should further be designed so as to prevent leakage of the injected liquid to the surrounding immersion liquid. Therefore, R4 is preferably designed to be larger than R5, in which case the hydraulic resistance of the bypass channel 15 is mainly impacted by R4. This prevents leakage in case of excessively large and excessively small operating distances. Still, the hydraulic resistance R5 of the second channel portion 152 is required to be able to create stagnation of flow (no flow condition across the first portion of the bypass channel 151).

To that aim, the hydraulic resistance R4 of the channel portion 151 may typically be between 2 and 100 times larger than the resistance R5 of the second channel portion 152. Yet, a ratio that is between 3:1 and 20:1 (e.g., 10:1) for R4:R5 was experimentally shown to be most suitable in practice. In variants, however, one may in fact specifically want to have R4<R5, e.g., in order to allow a liquid flow from the control channel 16 to enter the injection channel 12, so as to expand the volume of the hydrodynamic flow confinement, e.g., in case of large operating distances.

It is worth to remind that the hydraulic resistance of a channel (or a channel portion) is essentially determined by intrinsic feature of this channel (e.g., like dimensions, surface material, etc.). However, the hydraulic resistance typically scales with the flow rate, the pressure, the viscosity of the liquid, etc. Nevertheless, it remains that the bypass channels (or channel portions) may be suitably designed (e.g., dimensioned) so as to maintain certain desired relations between the resistances (e.g., to make sure that that R4>R5 and/or R3<R1, R2), for usual liquids and standard liquid flow rate/pressure, as used in MFPs in practice.

Figures 11A, 11B, 11C:
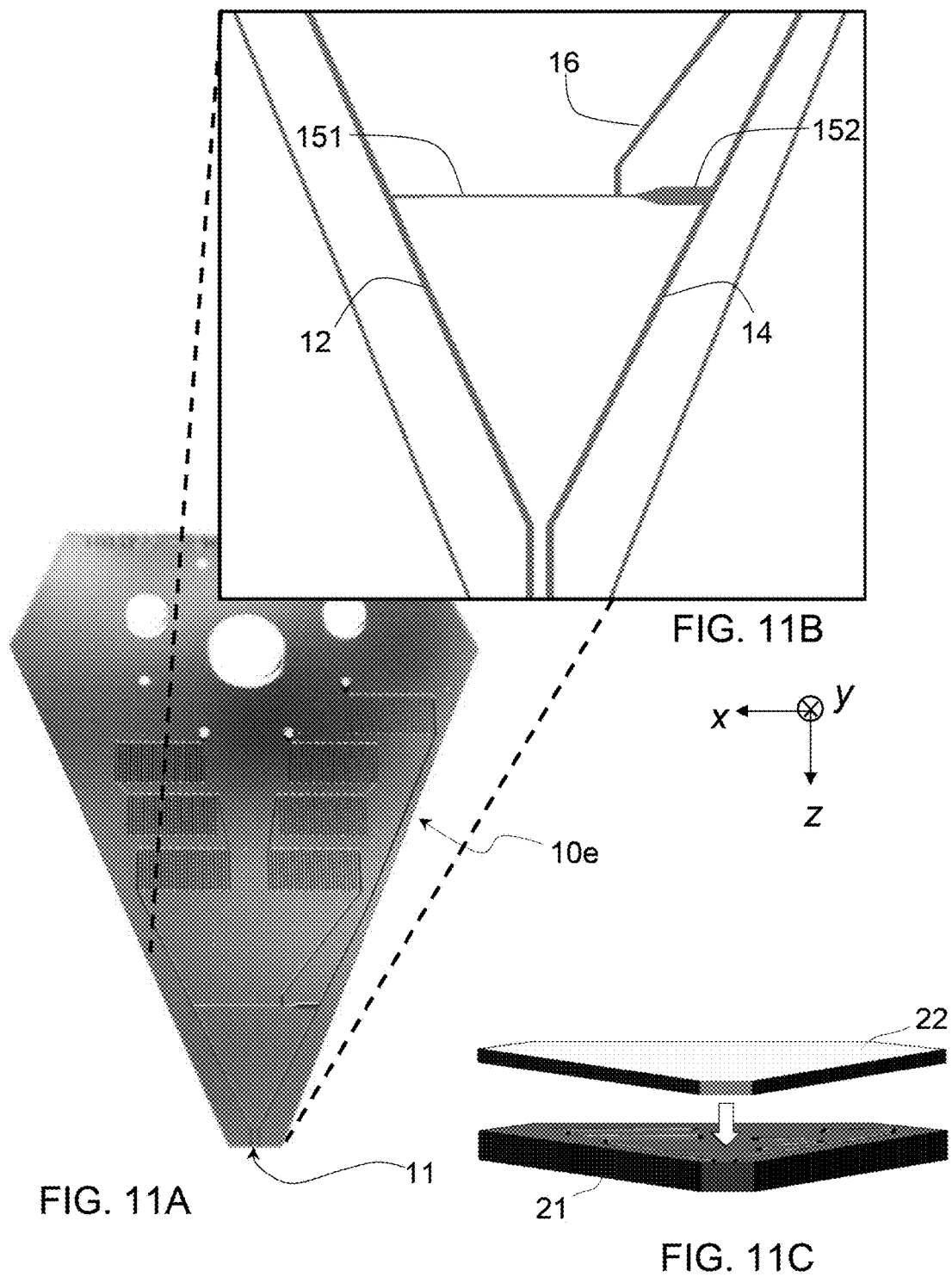
FIG. 11A shows a photograph of a layer of vertical probe head, which integrates the bypass and control channels, according to embodiments.
FIG. 11B shows a magnified portion of the channel structure about the bypass for the head of FIG. 11A.
FIG. 11C depicts an exploded, 3D view of the vertical head of FIG. 11A, showing how channels can be grooved on a lower layer and closed by an upper layer, as in embodiments.

As illustrated in FIGS. 11A-11B, the desired relations between the various hydraulic resistances may notably be obtained by adapting the average cross-sections of the channels. For instance, in the embodiment of FIGS. 11A-11C, the probe head 10e (here of a vertical type) is designed such that the first portion 151 of the bypass channel 15 has an average cross-section that is smaller than the average cross-section of the second portion 152 of the bypass channel 15. Varying the average cross-section of the channel portions allows to vary their hydraulic resistances, without requiring any change of surface material properties.

For example, and as illustrated in FIGS. 11A-11C, one may vary the widths of the channel portions, yet without varying the channel depth, which makes it relatively simple from the fabrication view point. I.e., in FIGS. 11A-11C, the first portion 151 and the second portion 152 of the bypass channel 15 have a same depth, while the first portion 151 has, on average, a smaller width than the second portion 152. Only the width of the channel portions 151, 152 is varied, whereas the etch depth can be kept constant.

As evoked earlier, the present MFP probes 1, 1a-1f shall preferably be configured to allow a hydrodynamic flow confinement (HFC) of the processing liquid injected through the aperture 112 and aspirated from aperture 114. Generally speaking, a HFC relates to a laminar flow of liquid, which is spatially confined within an immersion liquid (also called environmental liquid). I.e., the processing liquid need be injected via the first aperture 112 while re-aspirating liquid at the second aperture 114, at flow rates set so as to maintain a HFC of the injected liquid, between apertures 112 and 114. For this to be possible, certain conditions must be fulfilled, in terms of flow rates, dimensions of the apertures and relative distances therebetween, as known in the art.

In particular, by keeping the aspiration flow rate higher than the injection rate, e.g., at a defined ratio, a laminar flow path of processing liquid can be formed and confined within the immersion liquid 60. To that aim, a minimal distance between the injection and aspiration apertures is typically between 10 μm and 10 mm, and preferably between 30 μm and 2.0 mm. Also, the average diameter of the apertures 112, 114 need typically be between 5 and 250 μm. The probe may otherwise comprise or connect to suitable pumping means 41-43, to generate the required flow rates, as known per se.

More generally though, the present bypass and control concepts may be implemented in various types of MFP-like devices, irrespective of the device shape, materials used, aperture design and channel dimensions. Still, the channel and aperture diameters will typically be in the micrometers range (e.g., 5 μm to 250 μm).

For instance, suitable design parameters as used to obtain a device as shown in FIG. 11A may be taken as follows:

Bypass channel 15: 20 μm×100 μm (width×etched depth);

Length of bypass channel portion 151: 3 mm;
Length of bypass channel portion 152: 0.3 mm;
Injection flow rate: 1 μl/min;
Control flow rate: 1 μl/min;
Aspiration flow rate: 6 μl/min;
Average diameters of the channels 12, 14 and apertures 112, 114: 30 μm; and
Minimal gap between the injection and aspiration apertures 112, 114: 30 μm.

As illustrated in the above example, the first portion 151 has a length that is preferably larger than the length of the second portion 152 of the bypass channel 15. This too helps in achieving a larger hydraulic resistance for the first portion 151. The length ratio is preferably comprised between 2:1 and 20:1. It may for example be of 10:1, as in the example above.

Besides the implementation of the bypass channel 15, the design of the other channels 12, 14, 16 can be kept standard. In particular, the channels 12, 14, 16 will preferably have, each, a hydraulic resistance that is constant along their main channel extensions. That said, these channels 12, 14, 16 may have distinct resistances, as noted earlier. For example, the hydraulic resistance R3 of the control channel 16 may be smaller than each of the resistance R1 of the injection channel 12 and the resistance R2 of the aspiration channel 14.

For example, the hydraulic resistances R1, R3 of the injection channel 12 and the control channel 16 may be tuned to allow control of flow rates on the order of 1 μl/min, whereas the hydraulic resistance R2 of the aspiration channel 14 may be set to achieve flow rates on the order of 10 μl/min. The resulting ratio (10:1) can typically be used to obtain a HFC of injected liquid. More generally, the probe and the probe head may be configured to allow a HFC.

Several classes of embodiments can be contemplated, owing to that: (i) the bypass and control channels can be provided directly on the probe head ("on-head") or in a distinct module ("off-head"); and (ii) the head can be of the "vertical" or the "horizontal" type. Of particular advantage is that each of the "on-head" and "off-head" concepts are compatible with either type of probe head.

For instance, and as illustrated in FIGS. 1-8, and 11A-13, the bypass and control channels can be provided directly on the probe head. Namely, each of the injection channel 12, the aspiration channel 14, the bypass channel 15 and the control channel 16 extends within a body 18 of the probe head in that case. The bypass channel 15 fluidly connects the injection channel 12 to the aspiration channel 14, within the body 18 of the head.

As it may be realized, implementing the bypass-channels directly on the MFP head allows the system to react faster in case of failure. As a result, less processing liquid will escape the probe head and contaminate the immersion liquid and the substrate. The "on-head" approach is compatible with both a vertical probe head (where all relevant channels can be grooved on the same chip, as in FIGS. 11A-11C) and a horizontal probe head, as described below in detail.

Figure 12:
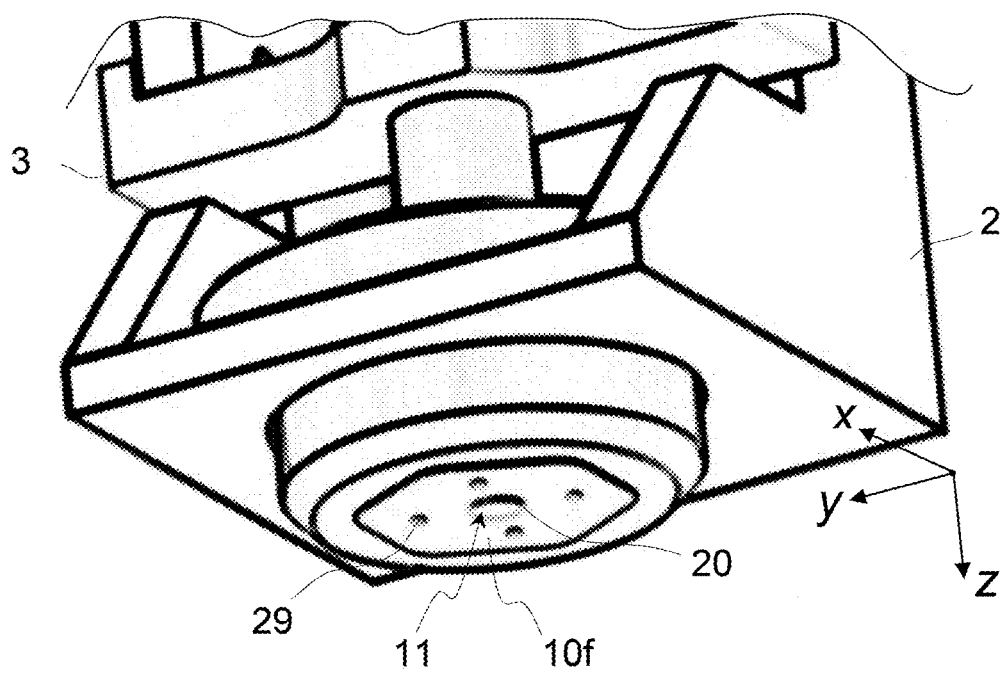
FIG. 12 is a 3D (partial) view of a microfluidic device that includes a "horizontal" probe head, according to embodiments.
Figure 13:
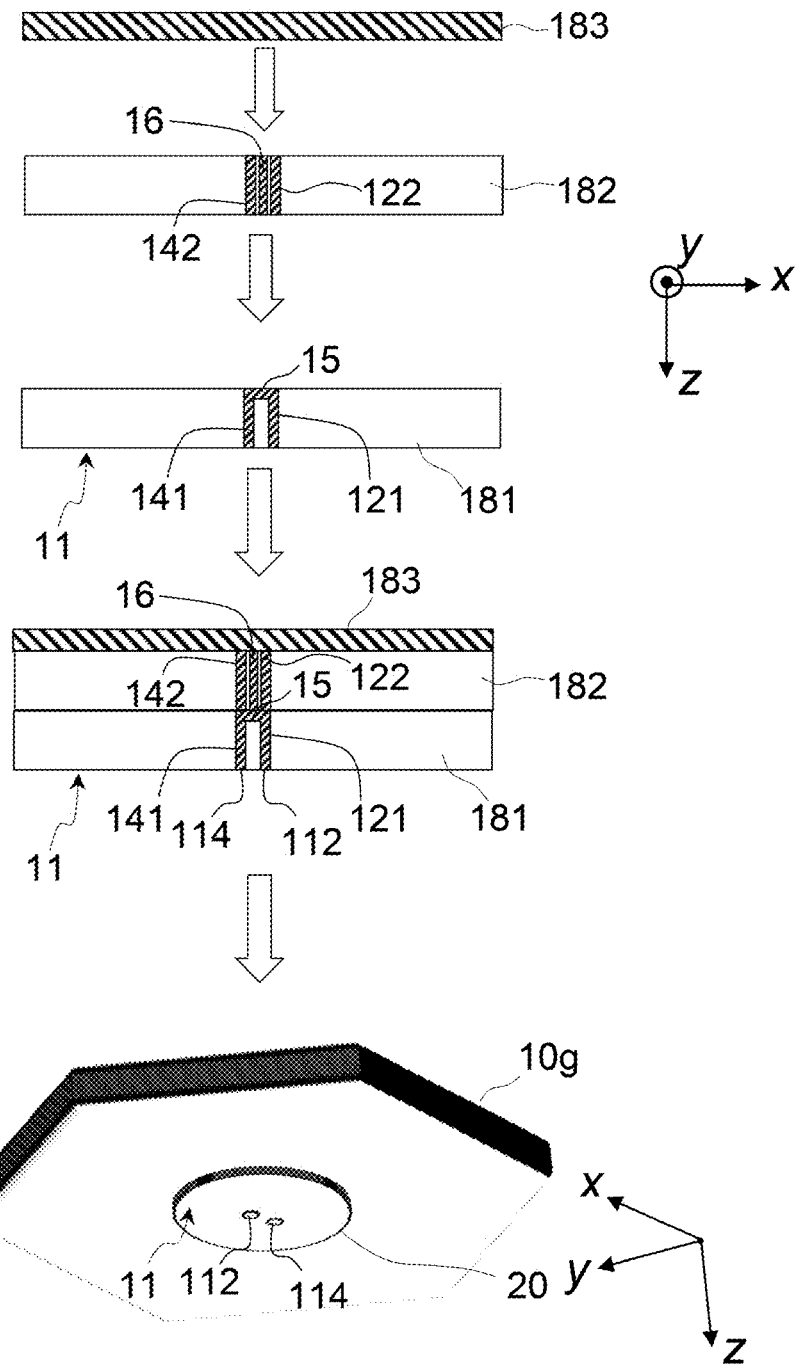
FIG. 13 illustrates the assembly of three layers (depicted in cross-section) to obtain a multilayer, horizontal probe head, which can be used in a device as depicted in FIG. 12.

In embodiments as illustrated in FIGS. 12 and 13, the MFP device includes a probe head 10f, 10g configured as a "horizontal" probe head. The MFP device 1f shown in FIG. 12 has a holder 2, designed for receiving a head 10f, the latter having a mesa 20, slightly protruding outwardly, so as to define a processing surface 11. Supporting posts 29 are provided on the head 10 for leveling purposes. A frame 3, on top of the holder 2, allows the head be mounted to positioning means that include, e.g., a goniometer on top (not shown), whereby the head 10 can be positioned (vertically, along z-axis) and rotated to a precise position.

The device 1f may further comprise usual equipment, such as, e.g., tubing ports, valves, pumping means) and otherwise be configured to allow a HFC of the processing liquid.

The device 1f may notably use a head 10g as shown in FIG. 13. This probe head 10g can be obtained through a simple fabrication process, using a few layers 181-183. The bypass channel 15 is implemented on the upper side of a layer 182 of the head, where the routing of the microchannels is done.

Namely, the probe head 10g shown in FIG. 13 comprises two layers 181, 182, including a control layer 182 and a routing layer 181. The bottom face of the control layer 182 covers the top face of the routing layer 181. The processing surface 11 is defined by the bottom face of the routing layer 181, opposite to the top face thereof. The apertures 112 and 114 are, each, defined on the bottom face of the routing layer 181.

The routing layer 181 comprises a first pair of through-vias 121, 141 extending through a thickness of layer 181, so as to form respective segments of the liquid injection channel 12 and the liquid aspiration channel 14. Such segments are in fluid communication with respective apertures 112, 114. The bypass channel 15 is defined on the top face of the routing layer 181.

The control layer 182 comprises a through-via (again extending through a thickness of layer 182), so as to form a segment of the control channel 16. The control layer 182 further comprises a second pair of through-vias 122, 142 (extending through a thickness thereof), so as to form additional segments of the injection channel 12 and the liquid aspiration channel 14, respectively. After assembly of the layers 181, 182, these additional segments 122, 142 make fluid communication with the first pair of through-vias 121, 141, respectively. Using such a fabrication concept, a bypass channel can easily be achieved, which connects channel 12, 14 (formed by respective segments 121, 122 and 141, 142) as well as the control channel 16, at the interface between the routing layer 181 and the control 182 layer.

At the final stages of fabrication, additional layers may be present, such as a capping layer 183, which closes the channels on top of the control layer 182. Furthermore, additional channel segments (not visible in FIG. 13) will typically be present in the layer 182, and, e.g., extend perpendicularly to the cutting plane of FIG. 13, so as to bring/evacuate liquid from the channel segments 122, 16, 142.

In other variants, the horizontal MFP heads can also be fabricated by machining a block material or thanks to 3D printing (not shown).

Another class of embodiments is now described, which relies on "off-head" implementation of the bypass and control channels, in reference to FIGS. 9 and 10. The embodiments of FIGS. 9-10 assume "vertical" heads, comparable to that of FIGS. 11A-11C, except that the heads 10c, 10d do not comprises any bypass or control channel, which are instead implemented in a separate module 30c, 30d.

Namely, the probe heads 10c, 10d comprise, each, a first segment 121 of the injection channel 12 and a first segment 141 of the liquid aspiration channel 14. The segments 121, 141 are in fluid communication with the first aperture 112 and the second aperture 114, respectively.

In addition, each of the probes 1c, 1d comprises a bypass module 30c, 30d, which is distinct from the probe heads 10c, 10d. The bypass channel 15 and the control channel 16 are provided in the bypass module 30c, 30d, which further comprises a second segment 122 of the injection channel 12 and a second segment 142 of the aspiration channel 14. In the bypass module 30c, 30d, the bypass channel 15 fluidly connects the second segment 122 of the injection channel 12 to the second segment 142 of the liquid aspiration channel 14.

Yet, the module 30c, 30d and the head 10c, 10d are arranged such that the channel segments 122, 142 are in fluid communication with the complementary segments 121, 141, respectively. This way, the bypass concept can be implemented outside the MFP head thanks to a module 30c, 30d that is nevertheless suitably connected to the MFP head. The functionality of the bypass-channels otherwise remains the same as when implemented on-chip. An off-chip configuration makes the bypass fabrication independent from the MFP head, which eases the fabrication and implementation as one can rely on existing probe heads, without substantially modifying the latter. Minor modifications (e.g., to obtain through-vias) may nevertheless be required, depending on the available heads.

The first and second segments of the injection and aspiration channels may be connected directly, assuming the head 10d is affixed to the bypass module 30d, as in FIG. 10, thanks to through-vias, which ensure fluid communication. That is, in FIG. 10, the probe head 10d comprises through-vias (denoted by black disks), extending transversely to the main plane of the chip (i.e., corresponding to layer 21 in FIGS. 11A-11C), from the end of the segments 121, 141. Corresponding through-vias (not visible) extend, in vis-à-vis, from a surface of the module 30d onto which the chip is fixed, toward channel segments 122, 142 provided in the bypass module 30d, so as to ensure fluid communication with corresponding channel segments 121, 141 on the chip, respectively.

A capping layer (not shown) comes to close the channel segments 121, 141. Similarly, a capping layer may close channel segments grooved on a body of the module 30d. This additional capping layer may be provided on either side of this body and may need to comprise though-vias if intercalated between the head 10d and this body. In variants, the module 30d is obtained by 3D printing, with channels segments extending within the body of the module. Through-vias would, again, be involved to ensure proper fluid communication.

In variants to FIG. 10, intermediate channel segments 12t, 14t may be used, e.g., provided as flexible tubes, as in FIG. 9, to connect channel segments 122, 142 in the bypass module 30 to the corresponding, on-chip channel segments 121, 141. Such variants allow existing concepts of vertical heads to be re-used, without any modification thereto. The variant of FIG. 10 allows somewhat faster reactivity, compared to FIG. 9, owing to the increased proximity of the bypass channel with the channel segments 121, 141. Yet, a substantially faster reactivity can be obtained if the bypass and control channels are both implemented directly at the probe head, as noted earlier.

Vertical probe heads 10, 10a-10e as shown in FIGS. 1-11C are particularly simple to fabricate. They may for instance be fabricated from two layers 21, 22 of material (e.g., silicon and glass, respectively), as illustrated in FIG. 11C. When used together with a bypass module, then only the channel segments 121, 141 need be grooved on a layer 21 (e.g., a silicon chip) of the head and closed by another layer 22 (e.g., glass). Thus, already existing concepts of vertical heads can advantageously be re-used, without the additional bypass and control channels need thereon. In the "on-head" approach, all channels 12, 14, 15, 16 can be grooved on layer 21, as assumed in FIGS. 11A-11C.

For completeness, we note that, although vertical probe heads are assumed in FIGS. 9-10, the off-head concept can equally be used with horizontal heads. Multilayer devices are typically relied upon in that case, as in FIG. 13, which involve materials such as, silicon, glass, PDMS or other elastomers, hard plastics, etc., as usual in the art.

Figure 14A:
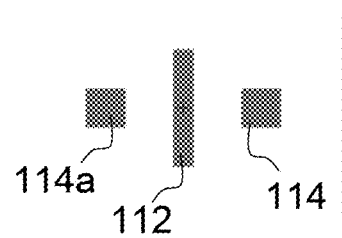
FIGS. 14A-C schematically depict views of different types of apertures that can be formed on processing surfaces of probe heads, as involved in embodiments.
Figure 14B:
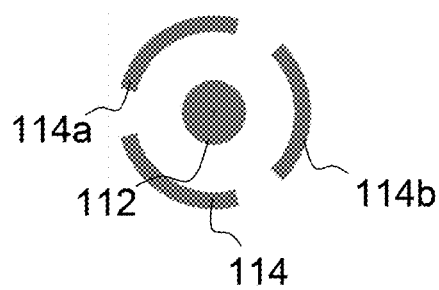

At present, referring to FIGS. 7, and 14A-14B, further embodiments are described, which concern a microfluidic probe 1a, wherein the processing surface 11 of the head 10a comprises multiple aspiration apertures 114, 114a, 114b. As better seen in FIGS. 14A-14C, a set of two (FIG. 7, 14A or more (FIG. 14B) apertures 114, 114a, 114b may be provided on the processing surface 11, where each aspiration aperture is arranged at a distance from the injection aperture 112. Consistently, and as depicted in FIG. 7, the probe 1a comprises a corresponding set of aspiration channels 14, 14a, which extend from a respective one of the apertures 114, 114a.

In such a case, additional bypass channels may advantageously be provided, as illustrated in FIG. 7, so as to avoid leakage of the processing liquid from any of the apertures. I.e., several bypass channels 15, 15a are provided in the probe, so as to fluidly connect the liquid injection channel 12 to a respective one of the aspiration channels 14, 14a. Consistently, two or more control channels 16, 16a fluidly connect to respective bypass channels 15, 15a.

Providing additional aspiration apertures as well as corresponding aspiration, bypass and control channels can be exploited to avoid leakage of the processing liquid into the immersion liquid. E.g., in case a topographical variation on the processed surface S starts blocking a given one 14a of the aspiration apertures (as illustrated in FIG. 7), another aspiration aperture 14, e.g., symmetrically positioned with respect to the blocked aperture 14a, may still ensure liquid aspiration, while excess of processing liquid injected from channel 12 can be diverted through the bypass 15a, as indicated by the curved arrow in FIG. 7. If all apertures happen to be blocked (not shown), then the processing liquid will be suitably diverted through both bypass channels 15, 15a, to avoid leakage of processing liquid.

FIG. 14A assumes symmetric (square) aspiration apertures. In variants to symmetric openings, one may use a curved slit or a set of curved slits for aspiration, as discussed below, in reference to FIGS. 14B, 14C, 15 and 16.

In embodiments such as depicted in FIGS. 14B-16, the probe head comprises one or more aspiration slits 114, 114a, 114b, each shaped so as to partly extend around the first aperture 112 on the processing surface 11. As a result, the injection aperture 112 is not completely surrounded by the slit(s) on the processing surface 11, which is typically defined on a mesa 20 of the probe head 10h, see FIG. 15. Each slit is partly coiled around the injection aperture (it may be either bent or curved).

Because the aspiration slit(s) extend(s) partly around the injection aperture, a degree of confinement of the injected liquid can be obtained, in normal operation of the head (assuming no failure). That is, injected liquid remains confined due to liquid aspirated at the slit, which forms a barrier extending around the injected liquid. The liquid barrier created by the liquid aspiration helps to improve homogeneity in the deposited liquid or particles thereof, such as cells. Meanwhile, the shape of the slit allows immersion liquid in the vicinity of the head to be aspirated via the slit. This further allows the flow velocity of the injected liquid to be set partly (if not essentially) independent from the aspiration flow, which, in turn, eases the operation of the head.

Note that, in that case, the bypass channel 15 may be partly circular, or, more generally, shaped, so as to ease fluid communication from the injection channel to the aspiration channel. Such a bypass channel may be provided at an interface between two layers, as in FIG. 13.

In other variants, such as depicted in FIG. 8, the probe 1*b* comprises several bypass channels 15, 15*a*, 15*b*, which all connect the same two channels 12, 14. That is, each of the bypass channels 15, 15*a*, 15*b* is arranged, e.g., directly in the probe head 10*b*, so as to fluidly connect the injection channel 12 to the aspiration channel 14. In embodiments such as depicted in FIG. 8, the probe further comprises a plurality of corresponding control channels 16, 16*a*, 16*b*, which fluidly connect to a respective one of the bypass channels 15, so as to form respective junctions therewith. To that aim, the probe 10*b* may be again configured as a multilayer probe head. Only the apparent, front-most layer is depicted in FIG. 8, for clarity, onto which is grooved the control channel 16. Additional control channels 16*a*, 16*b* (denoted by dashed lines in FIG. 8) can be defined at (hidden) interfaces between any two contiguous layers and connect to respective bypass channels 15*a*, 15*b*, thanks to through-vias (denoted by dashed circles in FIG. 8). Although a vertical head is assumed in FIG. 8, we note that the same concept can be implemented in a horizontal head.

Having multiple bypass channels allows gradual diversion of the processing liquid, when necessary. It further allows the device to have different working points, i.e., different bypass thresholds can be set, which makes it possible to cope with different failure scenarios with a same device, while operating the latter in a fully passive mode.

In variants (not shown), only one control channel is needed, which crosses all bypass channels, so as to further connect each of the additional bypass channels 15*a*, 15*b*. That is, a same control channel fluidly connects to each bypass channel in that case. Such variants typically require to adapt hydraulic resistances of the additional portions of the control channel.

Referring back to FIG. 1, the present probes may, in embodiments, be configured to operate in a constant liquid flow mode, and/or in constant pressure mode. That is, the system may be configured to operate in only one of these two modes, or in each of these two modes, it being noted that the probe is normally operated in one mode at a time. In constant liquid flow mode, a constant liquid flow is applied to each of the injection channel 12, the aspiration channel 14 and the control channel 16. In constant pressure actuation mode, a constant pressure is applied to each of these channels 12, 14 16. Applying a constant flow rate/pressure to the control channel 16 allows the probe to be passively operated, such that no active control and dynamic adaptation is required, even in case of failure. The system is fully passive as constant flow rates or pressures are applied to each of the channels 12, 14, 16.

To that aim, the present probe systems may include pressure sources 41, 42, and a vacuum source 43, as depicted in FIG. 1. In addition, liquid tanks (not shown) may be present, as usual in the art.

Moreover, a check valve (or a proportional valve) 44, and a flow sensor 45 may optionally be involved, to enable active or semi-active control, as assumed in FIG. 1. More generally, other active control means may be involved. In other variants, one may combine active and passive controls to enable additional functionality. For example, passive flow/pressure control in the bypass channel may be used to provide a sensitive feedback signal, which can be measured by a flow sensor 45 in the bypass supply line. This notably allows detection of an excessively large gap distance, tilt variations and blockages of apertures. Also, an active control element, i.e. a switch valve, in the bypass supply line may be used to make it possible to adjust, or even fully suppress the HFC without changing the injection and aspiration flow rates in the injection and aspiration channels 12 and 14. This proves to be very advantageous in applications where both a fast switching of liquids and a continuous flow of sample in the injection channel 12 are needed.

Referring to FIGS. 1, 3-6, and 15-16, another aspect of the invention is now briefly described, which concerns methods of operating a probe 1, 1*a*-1*f* such as described herein. Aspects of such methods have implicitly been described in reference to the devices 1, 1*a*-1*f* or their corresponding heads 10, 10*a*-10*h*. Essentially, such methods revolve around positioning the head 10, 10*a*-10*h* in proximity with a sample surface S to be processed (so as for the processing surface 11 to face the sample surface 5), and injecting processing liquid via an injection aperture while aspirating liquid from one or more aspiration apertures, to process the sample surface.

As described earlier, the sample surface S is typically immersed in an immersion liquid 60, so as for the probe head 10, 10*a*-10*h* to be at least partly immersed in the immersion liquid 60. In addition, the probes are preferably operated so as to maintain a hydrodynamic flow confinement of injected liquid between the injection aperture and the aspiration aperture(s).

The MFP head can either be kept static with respect to the sample surface 5, while depositing the processing liquid (e.g., containing cells), to obtain a homogeneous deposition, deposited as a spot onto the sample surface S. In variants, the MFP head can be scanned across the sample surface 5, e.g., to obtain a pattern, as discussed below and illustrated in FIG. 16.

Figure 14C:
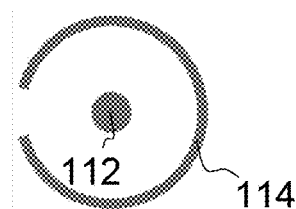
Figure 15:
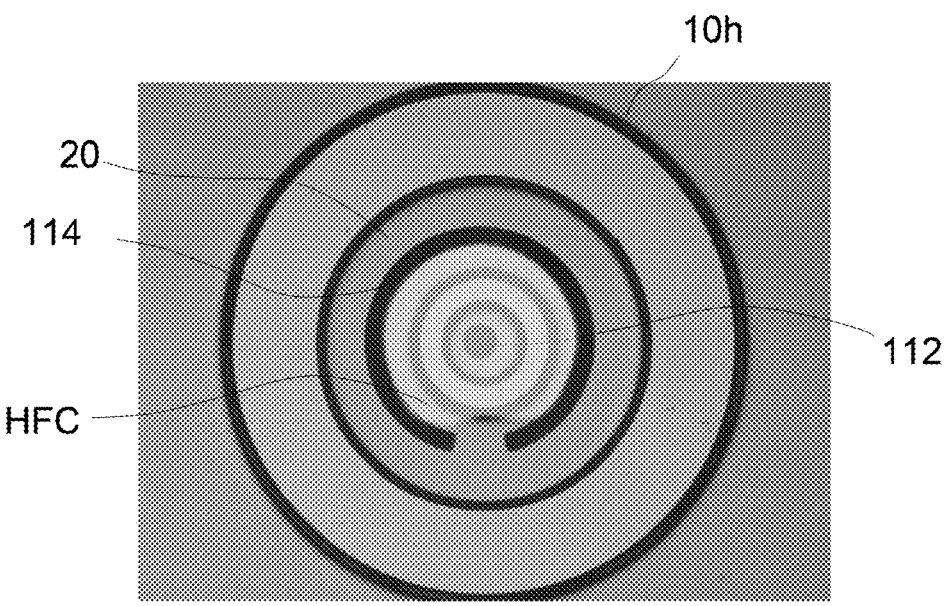
FIG. 15 is a photograph (taken with an inverted microscope through a glass slide) of the processing surface of a horizontal probe head, having apertures designed as in FIG. 14C, as involved in embodiments. The photograph shows a (whitish) liquid flow that is hydrodynamically confined between the injection aperture and the partly surrounding aspiration aperture.
Figure 16:
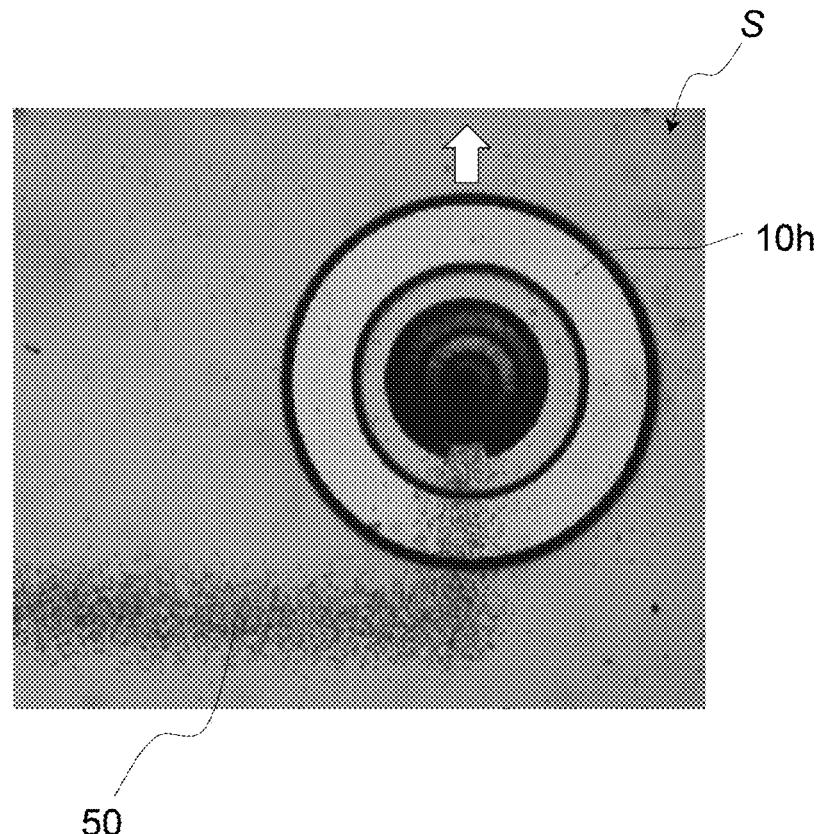
FIG. 16 is another photograph, illustrating how the NFP head of FIG. 15 can be scanned across a surface to deposit cells, according to embodiments.

For example, one may use an aspiration aperture shaped as a curved aspiration slit, as in FIG. 14C. In that case, and as illustrated in FIG. 16, the partial extension of the aspiration aperture slit around the injection aperture gives rise to a gap in the aspiration slit. Thus, the head can be scanned in a direction opposite to the gap with the gap located on the trailing edge, so as to minimize perturbations to the pattern of deposited cells. As further seen in FIG. 16, the head 10*h* is first scanned from left to right and then from bottom to top. For example, red blood cells 50 can be deposited onto the substrate during the scanning. The deposition of the cells can be performed over large distances (e.g., of 190 μm) and with a scanning velocity of, e.g., 50 μm per second. The device shown in FIG. 16 comprises a ring-shaped protruding structure of 30 μm high.

As previously described in reference to FIGS. 3-6, the present probes 1, 1*a*-1*f* may advantageously be used to cope with various failure scenarios. In particular, if one or each of the injection and aspiration apertures 112, 114 (114*a*, . . . ) happen to be blocked, due to the proximity of the probe head with the sample surface S, then liquid injected via the channel 12 can be (passively) diverted through the bypass channel 15 to be aspirated via the aspiration channel(s).

In other cases, e.g., when the distance to the surface of the sample becomes too large (FIG. 6), the liquid flowing in the control channel 16 can be (passively) diverted to flow through the injection aperture 112. Hence, the flow through the injection aperture 112 increases and the volume occupied by the injected liquid in the space between the probe 1 and the surface S protrudes further downwards and partially compensates for too large operating distances 6a.

In variants to passive operations, the liquid flow rate or the liquid pressure may be adjusted in the control channel 16, to provide (semi-)active control. This assumes that the liquid flow (or the pressure) is monitored in one or each channel 12, 14. Thus, if a liquid flow (or pressure) variation is detected, which is indicative of a failure, then flow/pressure can be adjusted in the control channel 16, as needed to compensate for the failure detected.

To that aim, a shut-off valve may be involved in the flow path of the control channel 16. This notably allows fast on/off switching of a HFC, without noticeably interrupting the injection liquid flow, and, in turn, improves the switching speed and stability of the HFC.

In addition, the footprint of the HFC can be varied by changing the flow rate/pressure in the control channel 16, as the overall injection to aspiration ratio changes (this ratio is defined as the sum of the injection flow and the control flow rate, divided by the aspiration flow rate). Such added flexibility may be exploited to generate patterns, modulate shear stress, or to reduce requirements on infrastructure. That is, instead of two high precision flow control lines for injection and aspiration, the latter two can be set coarsely and only one fine control is needed to set the exact shape of the HFC via the flow through the control channel 16.

In the simpler, passive solutions described earlier, the transition between normal operation and failure mode is typically set ex-ante, i.e., the transition threshold is set to a desired level by appropriately adjusting the flow/pressure in the control channel 16, i.e., prior to operate the probe. Then, the liquid flow rate (or the liquid pressure) is kept constant in the control channel 16 while processing the sample.

While the present invention has been described with reference to a limited number of embodiments, variants and the accompanying drawings, it will be understood by those skilled in the art that various changes may be made and equivalents may be substituted without departing from the scope of the present invention. In particular, a feature (device-like or method-like) recited in a given embodiment, variant or shown in a drawing may be combined with or replace another feature in another embodiment, variant or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated. For example, other materials than silicon or glass can be contemplated for layers 21, 22, such as, e.g., PDMS or other elastomers, hard plastics (e.g., PMMA, COC, PEEK, PTFE, etc.), ceramics, or stainless steel.

What is claimed is:

1. A method of operating a probe, the probe comprising:
   a probe head with a processing surface that comprises a first aperture and a second aperture;
   a liquid injection channel, which leads to the first aperture;
   a liquid aspiration channel, which extends from the second aperture, the liquid aspiration channel configured to aspirate liquid via the second aperture;
   a bypass channel, arranged so as to fluidly connect the liquid injection channel to the liquid aspiration channel; and
   a control channel, the control channel being configurable to match a pressure at a junction of the liquid injection channel and the bypass channel and a pressure at a junction of the control channel and the bypass channel and which fluidly connects to the bypass channel, hence forming a junction therewith, so as to define two portions of the bypass channel, the portions including:
   a first portion that extends from said junction to the liquid injection channel; and
   a second portion that extends from that same junction to the liquid aspiration channel,
   wherein the method comprises:
   positioning the probe head in proximity with a sample surface to be processed, so as for the processing surface to face the sample surface;
   adjusting a pressure in the control channel during a first operation to match the pressure at the junction of the liquid injection channel and the bypass channel and the pressure at the junction of the control channel and the bypass channel and adjusting the pressure in the control channel during another operation to enable liquid to pass from the liquid injection channel through the bypass channel to the liquid aspiration channel; and
   injecting processing liquid via the first aperture while aspirating liquid from the second aperture, to process the sample surface.

2. The method according to claim 1, wherein the method further comprises:
   blocking one or each of the first aperture and the second aperture, due to a proximity of the probe head with the sample surface processed, whereby processing liquid injected via the liquid injection channel passes through the bypass channel to get aspirated via the liquid aspiration channel.

3. The method according to claim 1, wherein the method further comprises one of:
   adjusting a liquid flow rate in the control channel; and
   adjusting a liquid pressure in the control channel.

4. The method according to claim 3, wherein
   adjusting the liquid flow rate or the liquid pressure in the control channel is performed prior to positioning the probe head in proximity with the sample surface, the liquid flow rate or the liquid pressure in the control channel being then kept constant while injecting processing liquid via the first aperture and aspirating liquid from the second aperture to process the sample surface.

5. The method according to claim 1, wherein:
   the probe head is positioned in proximity with the sample surface, onto which is an immersion liquid, so as for the probe head to be at least partly immersed in the immersion liquid; and
   liquid aspirated from the second aperture comprises immersion liquid.

6. The method according to claim 5, wherein
   the steps of injecting the processing liquid and aspirating liquid are performed so as to maintain a hydrodynamic flow confinement of injected liquid between the first aperture and the second aperture.

* * * * *